United States Patent [19]

Nagyvary

[11] 4,363,801

[45] Dec. 14, 1982

[54] METHOD FOR TREATING HYPERBILIRUBINEMIA

[75] Inventor: Joseph J. Nagyvary, Bryan, Tex.

[73] Assignee: The Texas A&M University System, College Station, Tex.

[21] Appl. No.: 232,640

[22] Filed: Feb. 9, 1981

[51] Int. Cl.$^3$ .................. A61K 31/725; A61K 31/73; C08B 37/08
[52] U.S. Cl. ........................................ 424/180; 536/20
[58] Field of Search ........................... 424/180; 536/20

[56] References Cited

U.S. PATENT DOCUMENTS

| | | | |
|---|---|---|---|
| 2,040,879 | 5/1936 | Rigby | 536/20 |
| 3,155,575 | 11/1964 | Doczi | 536/20 |
| 3,879,376 | 4/1975 | Vanlerberghe | 536/20 |
| 4,223,023 | 9/1980 | Furda | 424/180 |

OTHER PUBLICATIONS

Conn-Current Therapy 1979 W. B. Saunders, 1979 pp. 418–419.
Wenger, Chem. Abs. vol. 82, 1975 Ab. No. 80356b.
Sugano, The Amer. J. Clin. Nutrition, vol. 33, Apr. 1980, pp. 787–793.
Nagyvary, Nutrition Reports Int., vol. 20, Nov. 1979, pp. 677–684.

*Primary Examiner*—Anna P. Fagelson
*Attorney, Agent, or Firm*—Bill B. Berryhill

[57] ABSTRACT

Methods and preparations for treating hyperbilirubinemia utilizing chitosan salts as the active agent. A method of preparing the chitosan salts for oral administration in a liquid carrier is disclosed.

7 Claims, No Drawings

METHOD FOR TREATING HYPERBILIRUBINEMIA

BACKGROUND OF THE INVENTION

1. Field of the Invention

The present invention pertains to methods of treating hyperbilirubinemia and pharmaceutical and/or dietary preparations for such treatment. Specifically, the present invention pertains to a method of treating hyperbilirubinemia with an oral preparation in which chitosan is the active agent.

2. Description of the Prior Art

Hyperbilirubinemia is a condition of mammals, specifically humans, in which there are excessive amounts of bilirubin in the blood. Bilirubin is the chief pigment in human bile. It is derived from hemoglobin which is the red pigment of the red corpuscles. The main site of bilirubin is the liver. It is also made in the bone marrow, the spleen and the lymph glands.

Free bilirubin is the most toxic substance produced by the human body. In normal adults, however, the bilirubin is conjugated in the liver, i.e. converted to a nontoxic form known as bilirubin-glucuronide. Conjugation of bilirubin in the liver is catalyzed by the enzyme UDP-glucuronyl transferase. The conjugated form of bilirubin is water-soluble and can be excreted into the bile. While bile is passed into the intestines and the gall bladder, part of the bilirubin is converted into stercobilin and excreted in the feces. The remainder is reabsorbed in the bloodstream and of this portion the bulk returns to the liver to be reexcreted into the bile.

Hyperbilirubinemia frequently occurs in the first five days of life of a newborn baby and may clear up within seven to fourteen days. This condition known as "physiological jaundice of newborns" or "neonatal jaundice" is due to incomplete development of certain mechanisms of the body resulting in a decreased ability to conjugate bilirubin with glucronic acid. Specifically, the key enzyme, UDP-glucuronyl transferase, is not present in the newborn, requiring several weeks to be fully induced. As a result, the bilirubin cannot be conjugated and is retained in the body for some time. The condition is usually mild and self-limiting, though in premature infants, the hyperbilirubinemia may be more severe, last longer, and more frequently result in kernicterus. Kernicterus may result in severe neurological deficits, mental retardation, loss of IQ and even death.

It is estimated that as many as twenty-five percent of newborns are afflicted with this malady. In adults, hyperbilirubinemia, commonly referred to as "Gilbert's Disease", frequently results in death.

Neonatal jaundice has been successfully treated by complete blood transfusion, administration of phenobarbital and total body irradiation by visible light (phototherapy). Blood transfusion is quite inconvenient for babies. The most popular treatment is phototherapy. While phototherapy is effective, it is thought to be destructive of certain other body functions and perhaps harmful to a degree not known at the present time. Specifically, phototherapy has come under recent attack because of possible damage through photodynamic action possibly caused by bilirubin and its numerous photo-oxidation products.

SUMMARY OF THE INVENTION

In the present invention, hyperbilirubinemia is treated by oral administration of a preparation having a dietary influence, such influences having been ignored in the past. The method of treating comprises oral administration, to the affected patient, of a preparation including finely ground chitosan salt in a liquid carrier. The liquid carrier is preferably fruit juice. The preparation of the finely ground chitosan salt is important and a method of so preparing the chitosan salt for mixing with the liquid carrier is disclosed herein.

Chitosan is a natural product found in many fungi and yeast. Chitosan is also industrially manufactured from chitin, the hard material coating crustaceans, i.e. crawfish, crabs, lobsters, and shrimp. The polymer structure of chitin consists of N-acetyl-D-glucosamine units linked by Beta-(1-4) glycosidic bonds which impart to the material characteristics similar to that of cellulose. Chitosan is conventionally prepared by the alkaline deacetylization of chitin with concentrated sodium or potassium hydroxide at elevated temperatures. Depending upon the conditions of the deacetylization, chitosan with various degrees of deacetylization is obtained. In the most common products, the degree of deacetylization is between 70% and 90%. U. S. Pat. No. 4,195,175 discloses a process for the manufacture of chitosan.

The primary use of chitosan is in flocculating agents for water and waste treatment, chelating agents for removing traces of heavy metals from aqueous solutions, coating to improve dying characteristics of glass fibers, wet strength additives for paper, adhesives, photographic and printing applications, thickeners, formation of fibers and films, etc. The history and uses of chitosan and chitin are well documented in MUZZARELLI CHITIN (1977). In recent times, chitosan has been proposed for use in pharmaceutical preparations for inhibiting pepsin activity (U. S. Pat. No. 3,155,575) and in reducing the absorption of lipids such as triglycerides, fatty and bile acids as well as cholesterol and other sterols (U. S. Pat. No. 4,223,023). While chitosan has therefore been proposed for treatment of these ailments, no one has heretofore suggested its use in treating hyperbilirubinemia. Neither has chitosan been administered as a pharmaceutical or dietary preparation in the form of the present invention.

DESCRIPTION OF A PREFERRED EMBODIMENT

In accordance with a preferred embodiment of the invention, an oral preparation for the treatment of hyperbilirubinemia is prepared by mixing of finely ground chitosan salts in a liquid carrier substantially unaffected by precipitation. Before mixing with the liquid carrier, the chitosan salts are preferably prepared from a commercial grade of chitosan. As previously mentioned, commercial chitosan is usually prepared by the deacetylization of chitin. The degree of chitin deacetylization necessary to obtain a soluble product must be 80% to 85% or higher. Chitosan is thus not a single definite chemical entity but varies in composition depending on the conditions of manufacture. It may be equally defined as chitin sufficiently deacetylated to form soluble amine salts.

The rationale of the present invention is based on the recognition that chitosan, essentially a polyglucosamine, in a polycation and therefore should possess a strong binding for the anionic bilirubin. Chitosan is nondigestable and passes through the whole digestive tract. There are two avenues for bilirubin to be bound to chitosan: (1) when bile is released and (2) free bilirubin can equilibrate through the intestinal wall with the intestinal lumen. Thus, the toxic bilirubin and its derivatives are removed from the body with the feces which contains the complex of chitosan and the bile pigments. It is well understood that bilirubin itself undergoes bacterial modification in the colon. The main excreted metabolites of bilirubin are called urobilinogens.

It is preferable, in the present invention, to use a grade of chitosan which has been produced by boiling in sodium or potassium hydroxide from twenty-four to thirty hours. In preparing the oral preparation of the present invention, the commercial grade of chitosan is first dissolved in a weak acid such as acetic acid, citric acid, formic acid, tartaric acid and dilute mineral acids. For example, a weak acid comprising 4% acetic acid (40 mls/liter) has been found to be desirable. The amount of chitosan dissolved is preferably in a ratio of 5 to 50 grams per liter of weak acid solution. The crude chitosan and weak acid solution are then put in a blender for approximately 15 minutes to thoroughly agitate and pulverize the chitosan.

After the solution has been allowed to settle, it is decanted and shell frozen with dry ice and ethylene glycol. The frozen solution is then lyophilized (freeze dried). In such procedures, the solution is cryogenically frozen and then subjected to a high vacuum, causing the water to sublimate. Then the lyophilized chitosan salt resulting therefrom is pulverized into a finely ground powder for mixing with the liquid carrier.

Selection of the liquid carrier is extremely important. Chitosan salts have limited solubility in water. Furthermore, chitosan salts precipitate certain proteins in milk and milk cannot be used as the liquid carrier. Since the oral preparation of the present invention is primarily intended for the use of newborn babies experiencing neonatal jaundice, the liquid carrier must be one which is palatable to the infant. While any water-soluble salt of chitosan in molecular solution is acceptable, it may not be palatable unless flavoring agents, such as citrate and sucrose, are included.

The best liquid carriers found so far appear to be fruit juices, particularly citric juices. However, any other fruit juice, tomato, apple, pear, etc., may be used. The finely ground powdered chitosan salt is satisfactorily mixed with these fruit juices, having a tendency to adhere to the pulp particles therein. In addition, these juices are palatable to the infant and are readily ingested thereby. Suitable concentrations of chitosan salt in the fruit juice are 0.5 to 2 gm/200 ml for neonates and up to 5 gm/200 ml for adults. While the fruit juice preparation is almost essential for infants, adults suffering from hyperbilirubinemia may ingest the chitosan salts in other forms of diet. However, it should be in a preparation acceptable to the taste.

In studying the effects of the preparation of the present invention, experiments were conducted using the Gunn rat, an inbred species of rat having the same problem as newborn infants in that they lack glucuronyl transferase activity and have difficulty in conjugating and excreting bilirubin with the feces. As a result of a genetic defect, the serum bilirubin of the Gunn rat is 5-10 mg/100 ml, five to ten times greater than normal human levels. Normal levels of bilirubin present in human serum is in the range of 0.1-1.5 mg/100 ml, all neonates have a higher concentration and the dangerous level, 15-25 mg/100 ml, is not uncommon.

In a typical experiment, six rats were fed a semi-synthetic control diet for ten days. Thereafter, blood was obtained and serum bilirubin was determined to average about 10 mg/100 ml. Then, using the same rats, the diet was changed for second third and fourth feeding periods to diets containing 3%, 6% and 10% chitosan. Blood samples revealed lowering of the unconjugated bilirubin in serum by as much as 60% to 70% ($\pm 10\%$). Since the standard deviation was so small, the results of the experiment are extremely significant.

The bilirubin level in the neonate gradually drops with the development of body mechanisms. Due to the genetic defect in the Gunn rat, its high bilirubin level is substantially constant. Thus, the Gunn rat is a very conservative animal model of the neonatal jaundice experienced in newborns. Accordingly, it is predictable with certainty that similar or greater reduction in bilirubin in affected newborn babies can be expected. It is thus theorized that chitosan in amounts of from 1% to 12% of the affected infants's diet will result in substantial reduction of the amount of unconjugated bilirubin in the blood. This would represent a significant contribution to the treatment of hyperbilirubinemia.

Thus, the oral preparation, the method of preparing the oral preparation and the method of treating hyperbilirubinemia with the preparation of the present invention present most significant contributions to the treatment of this malady found in a significant number of newborn babies. Its use can be predicted to significantly reduce the neurological deficits and deaths due to this condition.

Not only is the oral preparation of the present invention effective, it is easily administered and relatively inexpensive. Furthermore, it is not expected to have the harmful side effects that may be present in treatments of the prior art, i.e. whole body exposure to visible light, phenobarbital and blood transfusions.

While specific preparations, methods of preparation and methods of administering the preparation are described herein, many others can be made without departing from the spirit of the invention. Accordingly, it is intended that the scope of the present invention be limited only by the claims which follow.

I claim:

1. A method of treating hyperbilirubinemia which comprises orally administering to the affected patient an amount of soluble chitosan effective to substantially reduce the amount of bilirubin in the blood.

2. The method of claim 1 in which said chitosan is administered as a water soluble salt in a solution of water with flavor additives.

3. The method of claim 1 in which said chitosan is administered as a chitosan salt in a solution of fruit juice.

4. The method of claim 3 in which the amount of chitosan salt administered is from 0.5 to 5 grams per 200 ml of fruit juices.

5. The method of claim 1 in which said chitosan is administered in an amount of from 1% to 12% of the patient's diet.

6. The method as set forth in claim 2 in which said chitosan salt is formed by: dissolving chitosan in a weak acidic solution; agitating said solution; lyophilizing said solution; and pulverizing the chitosan salts from said lyophilizing into a finely ground powder for mixing in said solution of water.

7. The method as set forth in claim 3 in which said chitosan salt is formed by: dissolving chitosan in a weak acidic solution; agitating said solution; lyophilizing said solution; and pulverizing the chitosan salts from said lyophilizing into a finely ground powder for said mixing in said solution of fruit juice.

* * * * *